(12) United States Patent
Corbett et al.

(10) Patent No.: US 11,615,793 B1
(45) Date of Patent: Mar. 28, 2023

(54) VOICE ASSISTANT CONFIGURED TO LEVERAGE INFORMATION FROM SENSING DEVICES

(71) Applicant: TELCARE MEDICAL SUPPLY, LLC, Concord, MA (US)

(72) Inventors: Jeremy J. Corbett, Nicholasville, KY (US); Khris Baker, Berea, KY (US); Jodi Augustyniak, Toledo, OH (US); Nathan Mitchell, Lexington, KY (US)

(73) Assignee: Centene Corporation, St. Louis, MO (US)

( * ) Notice: Subject to any disclaimer, the term of this patent is extended or adjusted under 35 U.S.C. 154(b) by 341 days.

(21) Appl. No.: 16/731,489

(22) Filed: Dec. 31, 2019

Related U.S. Application Data (60) Provisional application No. 62/787,573, filed on Jan. 2, 2019.

(51) Int. Cl.
| | |
|---|---|
| *G10L 15/22* | (2006.01) |
| *G16H 20/10* | (2018.01) |
| *G16H 80/00* | (2018.01) |
| *G10L 15/08* | (2006.01) |
| *G10L 15/30* | (2013.01) |
| *G10L 13/00* | (2006.01) |

(52) U.S. Cl.
CPC .............. *G10L 15/22* (2013.01); *G10L 13/00* (2013.01); *G10L 15/08* (2013.01); *G10L 15/30* (2013.01); *G16H 20/10* (2018.01); *G16H 80/00* (2018.01); *G10L 2015/088* (2013.01); *G10L 2015/223* (2013.01)

(58) Field of Classification Search
USPC .................... 704/235, 246, 247, 251, 252
See application file for complete search history.

(56) References Cited

U.S. PATENT DOCUMENTS

| | | | |
|---|---|---|---|
| 9,661,105 | B2 | 5/2017 | Sharma et al. |
| 10,200,834 | B2 | 2/2019 | Tran et al. |
| 10,347,255 | B1 | 7/2019 | Paul et al. |
| 10,366,336 | B2 | 7/2019 | Tur et al. |
| 10,460,215 | B2 | 10/2019 | Herold et al. |

(Continued)

OTHER PUBLICATIONS

Abdullah et al., Real time wireless health monitoring application using mobile devices, May 2015.*

(Continued)

*Primary Examiner* — Leonard Saint-Cyr (57) ABSTRACT

Methods, systems, apparatus, and computer-readable media for providing a voice assistant for to leverage information from sensing devices. In some implementations, one or more computers receive measurement data generated by a sensing device associated with a user. The one or more computers store the measurement data in association with an identifier for the user. The one or more computers obtain text of an utterance of the user detected by a client device associated with the user through a voice interface provided by the client device. The one or more computers access the measurement data associated with the user, and in response to obtaining the text of the utterance, generate a response to the utterance based on the text of the utterance and the stored measurement data. The one or more computers provide response data indicating the generated response.

20 Claims, 4 Drawing Sheets

(56) References Cited

U.S. PATENT DOCUMENTS

| | | |
|---|---|---|
| 2011/0040564 A1 | 2/2011 | Laughery et al. |
| 2012/0016678 A1 | 1/2012 | Gruber et al. |
| 2014/0005499 A1* | 1/2014 | Catt ................. A61B 5/746 |
| | | 600/301 |
| 2014/0187889 A1* | 7/2014 | Cohen .............. G16H 40/60 |
| | | 600/365 |
| 2014/0188398 A1* | 7/2014 | Cohen .............. G16H 40/60 |
| | | 702/19 |
| 2015/0356263 A1 | 12/2015 | Chatterjee et al. |
| 2016/0174853 A1* | 6/2016 | Cho ................. A61B 5/4277 |
| | | 600/301 |
| 2017/0293732 A1* | 10/2017 | Cohen ............... A61B 5/0022 |
| 2018/0177451 A1 | 6/2018 | Sahin |
| 2018/0316636 A1 | 11/2018 | Kamat et al. |
| 2018/0342329 A1 | 11/2018 | Rufo et al. |
| 2019/0133345 A1 | 5/2019 | Franz |
| 2019/0236205 A1 | 8/2019 | Jia et al. |

OTHER PUBLICATIONS

"Alexa Diabetes Challenge," 2017, 6 pages.

"Alexa: find Novo Nordisk voice-activated diabetes tech," PMLive, Jan. 3, 2018, retrieved from URL <http://www.pmlive.com/blogs/digital_intelligence/archive/2018/january/alexa_find_novo_nordisk_voice-activated_diabetes_tech_1215060>, 2 pages.

"Amazon's Alexa Now Brings the Ease of Voice-Activated Technology Directly to Members' Homes for Envolve Health's On.Demand Diabetes Management," Envolve Health, Jun. 17, 2019, retrieved from URL <Amazon's Alexa Now Brings the Ease of Voice-Activated Technology Directly to Members' Homes for Envolve Health's On.Demand Diabetes Management>, 3 pages.

"Eight expert healthcare industry trend predictions for 2018," Envolve People Care, Jan. 1, 2018, 13 pages.

"How voice assistants, like Amazon Alexa, are transforming the delivery of healthcare," Macadamian, Sep. 30, 2019, retrieved from URL <https://www.macadamian.com/learn/how-voice-assistants-like-amazon-alexa-are-transforming-the-delivery-of-healthcare/>, 6 pages.

"The Diabetic Epidemic," Envolve Health, 2019, 4 pages.

Baum, "Does Amazon Alexa have a future in diabetes management support?" MedCity News, Sep. 27, 2017, retrieved from URL <https://medcitynews.com/2017/09/amazon-alexa-future-diabetes-management-support/>, 11 pages.

Bulik, "'Alexa, help manage my diabetes.' That's what Merck and its contest finalists envision for the Amazon platform," FiercePharma, Jul. 19, 2017, retrieved from URL <https://www.fiercepharma.com/marketing/merck-taps-five-finalist-its-alexa-diabetes-contest-to-invent-voice-enabled-solutions>, 5 pages.

Castellino, "Sugarpod winds Alexa diabetes challenge," Medscape, Oct. 16, 2017, retrieved from URL <https://www.medscape.com/viewarticle/887083>, 13 pages.

Corbett, "Is AI for healthcare going too far?" HealthTech, Apr. 27, 2017, retrieved from URL <https://healthtechmagazine.net/article/2017/04/ai-healthcare-going-too-far>, 5 pages.

Ferguson, et al., "CARDIAC: an intelligent conversational assistant for chronic heart failure patient health monitoring," Virtual Healthcare Interaction: Papers from the AAAI Fall Symposium, 2009, pp. 8-12.

Google, "Smart Assistant," Diabetes: M: User's Guide, retrieved from URL <https://sites.google.com/view/diabetes-m-userguide/smart-assistant>, 3 pages.

Hoskins, "Talking diabetes tech: the future is now," Healthline, Mar. 16, 2017, retrieved from URL <https://www.healthline.com/diabetesmine/talking-diabetes-tech-alexa#1> , 12 pages.

Mutchler, "Creating an Alexa challenge for the real-world problem of diabetes," Voicebot, Jul. 25, 2018, retrieved from URL <https://voicebot.ai/2018/07/25/creating-an-alexa-challenge-for-the-real-world-problem-of-diabetes/>, 7 pages.

Seifert, "The future of the Home of the Future," The Verge, Sep. 10, 2018, retrieved from URL <https://www.theverge.com/2018/9/10/17832708/home-of-future-grant-imahara-smart-assistant-google-alexa>, 5 pages.

Wikipedia, "Amazon Alexa," retrieved from URL <https://web.archive.org/web/20181220183256/http://en.wikipedia.org/wiki/Amazon_Alexa> via Wayback Machine, available on or before Dec. 20, 2018, 21 pages.

Wikipedia, "Amazon Alexa," retrieved from URL <https://web.archive.org/web/20191212181003/http://en.wikipedia.org/wiki/Amazon_Alexa> via Wayback Machine, available on or before Dec. 12, 2019, 26 pages.

* cited by examiner

VOICE ASSISTANT CONFIGURED TO LEVERAGE INFORMATION FROM SENSING DEVICES

BACKGROUND

This application claims the benefit of U.S. Provisional Patent Application No. 62/787,573, filed on Jan. 2, 2019, the entirety of which is incorporated by reference herein.

BACKGROUND

Computers provide various forms of input and output. Some devices can provide a voice interface that allows a user to speak an input and receive information in response.

SUMMARY

In some implementations, conversational digital assistant functionality provides a voice interface to users, and is able to leverage data collected from one or more sensing devices. These sensing devices can be separate from the device that provides the voice assistant interface. For example, the voice assistant interface may be provided by an assistant device, e.g., a phone or a smart speaker, and a sensing device can be a separate device located in an office or the user's home. The sensing device can be configured to send data about sensed results to a server for the voice assistant system over a network, in some cases, doing automatically in response to capturing new measurement results. The server can then store the measurement data from the sensing device in association with a user related to the measurement, and use the stored measurement data to respond to later-received voice inputs from the user. In addition, the server can evaluate measurement results as they are received, to determine whether to trigger the presentation of one or more messages to the user through the voice interface (and/or a visual or other interface) of the assistant device. For example, in response to determining that a measurement from a sensing device related to a user satisfies a threshold, the server may generate a new notification, warning, or other message and cause the message to be presented by the assistant device for the user or another device, even without any voice input from the user to start the interaction session over the voice interface.

In some cases, the conversational digital assistant functionality provides a voice interface to users with diabetes. The digital assistant can provide a bridge that connects a user to a variety of devices and services, such as a remote server with glucose testing data, electronic medical records (EMR), devices for coaches and physicians, logistics systems (e.g., for scheduling delivery of test strips), emergency services, and so on. A user can access the digital assistant functionality through a device in their home or through a mobile device.

The assistant functionality can access test results provided by a blood glucose testing device to respond to user requests. The user can also submit data through the digital assistant, including their current blood glucose level. The user's glucose test results, or lack of glucose testing, can be used to provide customized messages and assistance to a user. For example, the digital assistant can answer a user's questions and provide information requested by a user, based on the user's glucose testing history or other medical history. In some implementations, the digital assistant initiates interactions with the user or other actions when the system detects certain conditions, such as a glucose test level outside a desired range or a user's lack of testing for a period of time. The conditions that the system respond to can be customized based on the user's history of testing and previous blood glucose levels, so that the system better responds to the user's specific needs. This comparison may result in the system providing a notification to the user through the digital assistant. The user can also ask the digital assistant questions regarding diabetes care and can use the digital assistant to contact the user's health coach, doctor, pharmacy or emergency services.

In one general aspect, a system includes: a server system comprising one or more computers, the server system being configured to store measurement data obtained for a user from a sensing device; a sensing device associated with the user, the sensing device being configured to automatically send measurement data to the server system indicating that a measurement has been performed and indicating results of the measurement; and a client device associated with the user, the client device providing a voice interface to the user. The server system is configured to perform operations comprising: obtaining text of an utterance received by the client device through the voice interface; generating a response to the utterance based on the measurement data; and providing data indicating the response to cause a synthesized speech response to be provided to the user through the client device.

In another general aspect, a system includes: a server system including one or more computers, the server system being configured to store glucose testing data for a user; a glucometer associated with the user, the glucometer configured to automatically send data to the server system indicating use of a glucose testing strip and results of glucose testing; a client device associated with the user, the client device providing a voice interface to the user; where the server system is configured to perform operations including: obtaining text of an utterance received by the client device through the voice interface; generating a response to the utterance based on the glucose testing data; and providing data indicating the response to cause a synthesized speech response to be provided to the user through the client device.

In some implementations, obtaining the text of the utterance includes obtaining, over a communication network, a transcription of the utterance generated through automatic speech recognition performed by a third-party voice processing server.

In some implementations, the operations include: storing, by the server system, data that indicates a coach assigned to assist the user; identifying, based on the presence of one or more keywords in the utterance, determining an electronic address for the coach assigned to assist the user; and in response to receiving the data indicating the utterance, initiating a call between a device associated with the coach and a device associated with the user.

In some implementations, the operations include: causing, by the server system, the client device to output a prompt to the user; obtaining data indicating a transcription of a spoken response to the prompt; extracting, from the transcription, data indicating one or more of a glucose testing time, a glucose testing result, a symptom experienced by the user, or a mood of the user; and updating records for the patent based on the extracted data.

In some implementations, the operations include: storing data indicating a predetermined set of milestone conditions related to glucose testing; determining, based on stored glucose testing records for the user, that at least one of the predetermined set of milestone conditions has occurred; and based on determining that the at least one milestone condition has occurred, providing an incentive corresponding to the at least one milestone condition.

In some implementations, the at least one milestone condition includes accessing functionality provided by the server system at least a minimum level.

In some implementations, the operations include: determining a time for glucose testing for the user; determining that the server system has not received an indication of a glucose test for the determined time; and based on determining that the server system has not received an indication of a glucose test for the determined time, initiating a message to the client device that reminds the user to perform a glucose test.

In some implementations, determining the time includes determining the time based on an estimate of mealtimes for the user or a history or pattern of glucose testing times for the user.

In some implementations, the operations include: receiving data indicating a blood glucose level determined using the glucometer; determining that the blood glucose level is outside a range; and in response to determining that the blood glucose level is outside the range, initiating a communication to a coach, medical service provider, or emergency response provider.

In some implementations, the operations include: accessing data indicating a treatment regimen that includes one or more medications prescribed for the user; determining that the server system has not received data indicating a needed glucose test for the user; and in response to determining that the server system has not received data indicating a needed glucose test for the user, providing a message that reminds the user to take the one or more medications according to the treatment regimen or asks the user whether the user took the one or more medications.

In some implementations, the text of the utterance includes data indicating a time of a glucose test and/or a result of a glucose test, and wherein the operations include updating glucose testing records for the user, based on the text of the utterance, to indicate the glucose test and/or result of the glucose test.

In some implementations, the operations include: storing data indicating a threshold period of time for glucose testing for the user; determining that glucose testing has not occurred for a time period of at least the threshold period of time; and in response to determining that glucose testing has not occurred for a time period of at least the threshold period of time, initiating an interactive voice communication with the user through the client device.

In some implementations, the interactive voice communication is a call to a medical professional or a call with an automated voice response system using the voice interface.

In some implementations, the threshold period of time is customized for the user based on the stored data indicating the user's history of glucose testing.

In some implementations, the operations include: evaluating the stored data indicating glucose testing history of the user to determine one or more patterns in the timing of glucose testing by the user; determining that a length of time since a most recent glucose test deviates from the one or more patterns; in response to determining that the length of time since the most recent glucose test deviates from the one or more patterns, initiating a message to the user through the client device.

In some implementations, the operations include: determining that a glucose reading for the user exceeds a threshold, wherein the threshold is a predetermined threshold or a threshold that is customized for the user; and in response to determining that the glucose reading for the user exceeds a threshold, performing one or more of: initiating a call or message to a diabetes coach for the user; initiating a call or message to a doctor for the user; initiating a call or message to emergency services; or initiating a communication to the user that requests information about what the user ate or whether the user took a medication.

In some implementations, the operations include: tracking usage of glucose test strips based on data from the glucometer indicating of testing performed by the glucometer; and scheduling shipments of test strips to the user, wherein the timing of shipments and amount of test strips in the scheduled shipments are determined based on the tracked usage for the user.

In some implementations, the operations include: providing, to a user, a message indicating an expected arrival date for a shipment of test strips and an amount of test strips in the shipment.

In some implementations, the operations include: causing the client device to output a message to the user, the message requesting a user prediction of glucose test results of a future glucose test; receiving text of a spoken in response to the request that indicates a user prediction of glucose test results; receiving data indicating actual glucose test results for a glucose test performed after the user provided the user prediction; comparing the actual glucose test results with the user prediction of glucose test results; determining, based on the comparison, whether the user prediction is within a predetermined range of the actual glucose test results; and based on determining whether the user prediction is within the predetermined range, varying an amount of a reward provided to the user.

In some implementations, the operations include: sending data to the client device causing the client device to initiate a request for a location of or contact information for the user; receiving, from the client device, data encoding an utterance of the user following output of the request by the client device; using automated speech recognition to extract, from the data, a location or contact information for the user; and storing the extracted location or contact information in a user profile for the user.

In some implementations, the operations include: determining a location of the user; and generating or adjusting the message based on the location. In some implementations, the location of the user is determined from an utterance of the user, a profile for the user, an IP address of the client device, or a GPS receiver of the client device.

In some implementations, generating or adjusting the message based on the location includes: determining current or forecasted weather for the location and generating or adjusting the message based on the current or forecasted weather; or determining a diet associated with the location and generating or adjusting the message based on the determined diet.

In some implementations, determining the diet includes determining the diet based on a diet for a population that resides in the location; or wherein the location is a location of a restaurant, and wherein determining the diet is based on a menu for the restaurant.

In another general aspect, a method performed by one or more computers includes: receiving, by the one or more computers, measurement data generated by a sensing device associated with a user, the measurement data being sent by the sensing device automatically in response to a measurement to indicate performance of the measurement and results of the measurement; storing, by the one or more computers, the measurement data in association with an identifier for the user; obtaining, by the one or more computers, text of an utterance of the user detected by a client device associated with the user through a voice interface provided by the client device, the text being generated by an automated speech recognizer; accessing, by the one or more computers, the stored measurement data associated with the user; in response to obtaining the text of the utterance, generating, by the one or more computers, a response to the utterance based on the text of the utterance and the stored measurement data; and providing, by the one or more computers, response data indicating the generated response, the response data being configured to cause a synthesized speech output to be provided to the user through the client device.

In another general aspect, a method performed by one or more computers includes: receiving, by the one or more computers, glucose testing data generated by a glucometer associated with a user, the glucose testing data being sent by the glucometer automatically in response to a glucose test to indicate use of a glucose testing strip and results of the glucose test; storing, by the one or more computers, the glucose testing data in association with an identifier for the user; obtaining, by the one or more computers, text of an utterance of the user detected by a client device associated with the user through a voice interface provided by the client device, the text being generated by an automated speech recognizer; accessing, by the one or more computers, the glucose testing data associated with the user; in response to obtaining the text of the utterance, generating, by the one or more computers, a response to the utterance based on the text of the utterance and the stored glucose testing data; and providing, by the one or more computers, response data indicating the generated response, the response data being configured to cause a synthesized speech output to be provided to the user through the client device.

Other embodiments of these and other aspects disclosed in the application include methods, systems, and apparatus, including computer-readable media storing software instructions that configure one or more computers to perform the functions disclosed herein.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
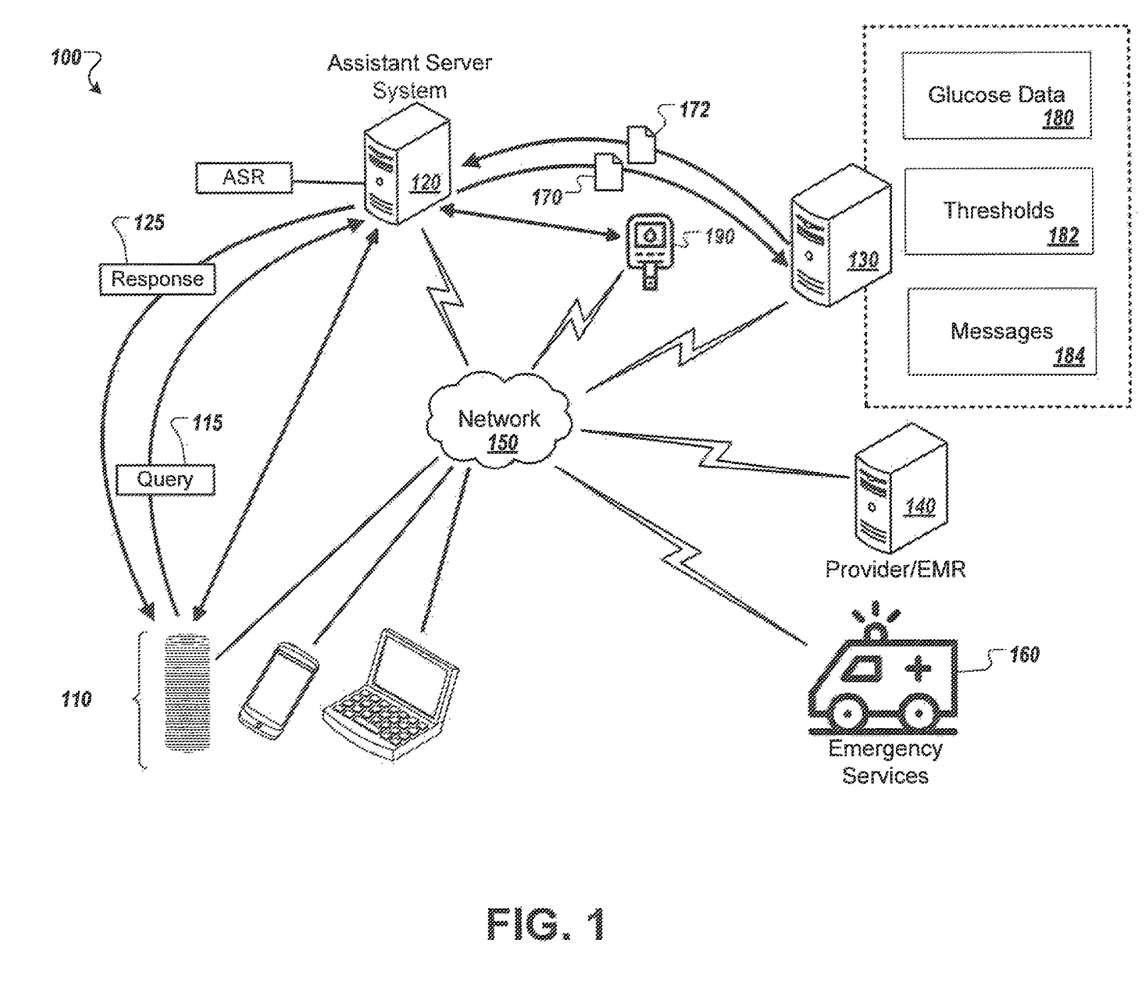
FIG. 1 is a diagram that illustrates an example of a system implementing a digital assistant.

FIG. 1 is a diagram that illustrates an example of a system 100 for implementing a digital assistant. The system 100 can be used to leverage the measurement data of one or more sensing devices to generate responses over a voice interface and to initiate communication sessions over a voice interface. The system 100 can be used to provide voice interface services for a variety of situations and applications. These include, but are not limited to, interactions related to medical conditions (e.g., diabetes, heart disease, etc.). Other uses that are outside of medical care, such as entertainment, manufacturing, office productivity, and so on, can be made using the same techniques. In general, the techniques herein can be used to leverage the data from sensing devices, especially sensing devices that may not be in communication with a user device or assistant device providing the voice interface.

The system 100 includes a glucometer 190 that a user can use to submit their blood glucose levels. The system 100 includes a user device 110 that a user can use to access digital assistant functionality. The user device 110 communicates with an assistant server system 120 over a network 150. The network 150 can include public and/or private networks and can include the Internet. The assistant server system 120 also communicates with a back-end server 130 to allow the storing and access of data for the user. The assistant server system 120 can also communicate with other servers, such as a medical provider system and/or an electronic medical record (EMR) system 140 ("medical provider/EMR system 140") through the network 150. The assistant server system 120 can also communicate with emergency services 160 through the network 150.

Glucometer 190 is a glucose meter that receives glucose testing strips containing a user's blood. Glucometer 190 then determines the approximate concentration of glucose in the user's blood (i.e., test result). Glucometer 190 communicates with the assistant server system 120. The glucometer 190 can communicate with the assistant server system 120 directly so that any test results are not tampered with. In some implementations, glucometer 190 can communicate with the assistant server system 120 through network 150. When glucometer 190 determines a test result, the test result is automatically sent to the assistant server system 120. Automatically sending the test results to the assistant server system 120 may also help to prevent tampering and may help the system 100 to provide more accurate notifications to the user (see, e.g., FIG. 2C).

Although various examples below relate to interactions to support diabetes care, this is only exemplary. For example, although the glucometer 190 is included as an example, any of various other sensing devices may be used to capture and send measurement data that is then used by the server system 120. For example, the sensing device may instead be a different type of device measuring physiological parameters, for example, a blood pressure cuff, a scale, a pulse oximeter, etc. In applications outside the medical field, the sensing device may include a temperature sensor, a light sensor, a sensor configured to indicate status of a device (e.g., whether a device is on or off, whether a door is open or closed, etc.), and so on.

The user device 110 can be a computing device, e.g., a smart speaker, a mobile phone, smart phone, personal digital assistant (PDA), music player, e-book reader, tablet computer, a wearable computing device, laptop computer, desktop computer, or other portable or stationary computing device. The user device 110 can feature a microphone, physical buttons, keyboard, touchscreen, or other interface that enables the user to provide inputs to the user device 110.

The assistant server system 120 can include one or more computers. In some implementations, one or more computers of the assistant server system 120 may communicate with the user device 110 and one or more other computers may perform other tasks such as speech recognition, text-to-speech processing, analysis of user requests, and so on.

The back-end server 130 is used to store information about the user, including glucose data 180, predetermined thresholds 182, and messages 184. Glucose data 180 may be initially populated by information accessed through the medical provider/EMR system 140. Predetermined thresholds 182 may include both thresholds for blood glucose level and timing thresholds. Predetermined threshold 182 may be populated by information accessed through the medical provider/EMR system 140, may be preset for all users, or may be determined by the system 100 for that particular user. In some implementations, the messages 184 have elements that are preset, such as templates for responses to typical queries or requests that are expected from users. The templates can include fields that the assistant server system 120 can fill in based on a user's glucose testing history to provide a relevant result to the user. In some implementations, at least some of the messages 184 are dynamically generated in other ways.

The network 150 can include public and/or private networks and can include the Internet.

In the example of FIG. 1, a user can make a request, such as a request/query 115, to a digital assistant using the user device 110. The request/query 115 is provided to the assistant server system 120, which first performs speech recognition on the request/query 115 and then determines an action requested by the user. Based on the action requested by the user, the assistant server system 120 may need to access data, such as the glucose data 180, the thresholds 182, and/or the messages 184, located in back-end server 130. The assistant server system 120 does this by sending a request or data packet 170 (here a request) to the back-end server 130. The back-end server 130 provides the requested data to the assistant server system 120 through a data packet 172. The assistant server system 120 then analyzes the requested data packet 172 and determines which message to send to the user. The assistant server system 120 may modify a predetermined message such that it incorporates particular data, such as a blood glucose level, the current time, a previous time associated with a blood glucose reading or a missed blood glucose test, .etc. The assistant server system 120 then sends this predetermined or modified message to the user in a response 125.

In the example of FIG. 1, a user can also submit data to the system 100 through the digital assistant using the user device 110. Such data can include blood glucose level results of the user. The data is provided to the assistant server system 120, which categorizes the type of data. For example, the assistant server system 120 may categorize that the data as blood glucose data. The assistant server system 120 then sends a request or data packet 170 (here a data packet) to the back-end server 130 to update the glucose data 180, the thresholds 182, and/or the messages 184. This user submitted data may also be sent by the assistant server system 120 to the medical provider/EMR system 140 to update their records.

Based on the request/query 115 or the data submitted by the user, the assistant server system 120 may determine it necessary to contact the user's medical coach, the user's doctor, or emergency services 160. The assistant server system 120 will determine if any such contact is necessary by comparing, for example, a user's submitted blood glucose level and comparing it with predetermined thresholds 182 stored on the back-end server 130. Such a comparison may result in assistant server system 120 determining that no contact is necessary, that only contact with the coach is necessary, that only contact with the doctor is necessary, that only contact with emergency services is necessary, or a combination of two or more of the contacts is necessary. If such contact is determined necessary, the assistant server system 120 will send a request or data packet 170 (here a request) to the back-end server 130 for the messages 184 related to contacting one or more of the contacts. The assistant server system 120 will receive a data packet 172 from the back-end server 130 and then modify the message if necessary before sending it to the user's coach, the user's doctor, or emergency services.

The user can provide data to the system 100 through the digital assistant on the user device 110. The data may include, for example, blood glucose testing results submitted by the user when they were not able to test their blood with the glucometer 190. The user may also submit other data, such as how they are currently feeling, what they have eaten today, and where they are located. The system 100 may induce the submission of data by providing the user a survey to fill out through the digital assistant. This survey can be used to customize the user's experience with their digital assistant. A survey may be used to acquire information about the user's lifestyle, demographics, location, health goals, analyze how the user engages with the user device 110, and/or other information. This information can be used to create a customized plan for the user and/or can be used to adjust the content the user receives. When a user submits data, that data is sent to the server system and stored. That data may be compared to other data associated with the user on the server system. The comparison may be carried out on the server system or locally on the user device 110, which has access to the server system through a network. Based on the comparison results, the system 100 may determine a message for the user and then send that message to the user through a notification. Based on the comparison results, the system 100 may also, or alternatively, contact the user's medical coach, doctor, and/or emergency services.

Self-reporting by the user is not the only way that the system 100 acquires data on the user. As discussed above, the system 100 can automatically receive blood glucose results through glucometer 190, e.g., as tests are performed and results are acquired. In some implementations, the system 100 is connected to the medical provider/EMR system 140. This connection can be a wireless network connection between the assistant server system 120 and the medical provider/EMR system 140. This connection can be a wired connection between the assistant server system 120 and the medical provider/EMR system 140. Data from the medical provider/EMR system 140 may be copied and stored on the assistant server system 120. Such data may include, for example, how often a user is supposed to test their blood glucose level (e.g., set or recommended by a doctor or other medical professional for the user, automatically recommended by the assistant server system 120 based on characteristics and/or behaviors of the user, or the like), blood glucose thresholds (e.g., that may be general for all users, may be specific to a group of users having specific characteristics and/or behaviors, may be specific to the user based on their characteristics and/or behaviors, or the like), and where the user is located (e.g., based on data provided by a GPS unit of the user device 110 or another computing device of the user, through the IP address of the user device 110, and/or based on information self-reported by the user).

The server system 120 can store received glucose testing results and other data about a user in association with an identifier for the user, e.g., an identifier that uniquely specifies the user's identity. This identifier can be associated with (e.g., mapped to) other identifiers, such as device identifiers for the user's user device 110, the user's glucometer 190, and so on. For example, the server system 120 can maintain a table or other data structure showing the correspondence between user identifiers and corresponding user devices, glucometers, and so on. When the glucometer 190 automatically sends glucose testing data, the glucose testing data message can include an identifier, such as the user identifier and/or an identifier for the glucometer 190, allowing the correct user identity, user account, and/or storage field(s) to be located and updated with the new data.

In some implementations, data gathered by the digital assistant of the user device 110, such as self-reported data or automatically acquired data, is provided to the medical provider/EMR system 140, e.g., over the network 150. The medical provider/EMR system 140 may use this data to update the user's medical records. The data can be provided to the medical provider/EMR system 140 by the assistant server system 120 or, in some implementations, by the digital assistant of the user device 110. The data sent to the medical provider/EMR system 140 may be encrypted, e.g., by the assistant server system 120, by the user device 110, or by the digital assistant of the user device, prior to being sent to the medical provider/EMR system 140.

The system 100 can use the acquired data in a number of ways. For example, the system 100 may use the location data, whether self-reported, acquired through the user's response to a survey, acquired through the IP address of the user device 110, acquired through a GPS unit of the user device 110 or the GPS unit of another computing device, or through the medical provider/EMR system 140, to generate or select one or more messages and/or recommendations. For example, using acquired location data, the assistant server system 120 may look up the weather in the user's area and determine how the current or expected weather could impact blood glucose testing, and/or determine a message to send to the user based on the weather. For example, if the assistant server system 120 determines that the weather is going to be warm and sunny in the user's area, the assistant server system 120 may send a message to the user stating "It's going to be sunny today. Perfect weather to go outside for a walk." As another example, if the assistant server system 120 determines that thunder storms are expected later in the day in the user's area, the assistant server system 120 may send a message to the user stating "Thunder storms expected today during your usual run. Better to use the treadmill today."

In determining how the current or expected weather could impact blood glucose testing, the assistant server system 120 may refer to a lookup table to determine the effect of current or expected weather conditions on blood glucose testing. The lookup table may take into account the characteristics of the user such as, for example, their weight, age, sex, and/or behaviors (e.g., how often they exercise, how often they eat, what they eat, how often they take insulin injections, how consistently they take their insulin injections, etc.). Alternatively, the assistant server system 120 may calculate the effect of current or expected weather conditions on blood glucose testing using one or more algorithms. These algorithms may take into account the weight, age, sex, and/or behaviors of the users as well as the current or expected weather conditions.

Similarly, the system 100 can also use the weather information (including pollen count) to send general health reminders. For example, the system 100 may send a message to all users in a given area that, "If you have allergies, remember the pollen count will be high in your area this week." The system 100 can also use location information to look at the common types of meals in the area (e.g., a diet) where the user is located and how those meals may impact the user's blood glucose level. Similarly, the system 100 may create a food access database and/or access one or more food access databases for a given area in order to determine the availability of food in a given area (e.g., a diet). This food availability information can be used to anticipate an impact on a user's blood glucose level and could also be used, for example, in addressing Social Determinants of Health (SDOH). Based on the user's location, the system 100 may send the user a message directing them to a recommended food source. This recommendation may also be prompted by a received blood glucose level indicating that the user should eat something. For example, the system 100 may send a user a message stating "The nearest fresh food market is only 1.2 miles away."

In generating a message and/or a recommendation, the system 100 (e.g., the assistant server system 120), may refer to one or more lookup lists. There may be multiple lookup lists where one or more lookup lists belong to different categories of messages or recommendations. For example, there may be a lookup list for weather, a lookup list for restaurants or types of restaurants, a lookup list for food or types of food, a look up list for reminders or notifications. As an example, a weather lookup list may include a number or predetermined messages or portions of predetermined messages such as a predetermined rain message or a predetermined portion of a rain message with one or more fields to be filled in, sunny weather message or a predetermined portion of a sunny weather message with one or more fields to be filled in, a storm message or a predetermined portion of a storm weather message with one or more fields to be filled in, etc. Similarly, there may be a lookup list for restaurant or food recommendations. The fields may include, for example, the specific area where the user is located (e.g., city, county, etc.), the current or expected temperature, the current or expected humidity, the current or expected chance of the corresponding weather (e.g., percent chance of rain, sunny weather, thunder storm, etc.), the current or expected pollen count, or the like.

A restaurant lookup list may include restaurants in the user's area (e.g., in the user's listed city, within 5 miles of the user's current location, within 10 miles of the user's current location) and may, in some implementations, be dynamically updated based on changes to the user's location. Each option in the restaurant lookup list may also include a type of restaurant, one or more menu items provided by the restaurant, and/or any dietary restrictions that are relevant to food provided by the restaurant (e.g., if the restaurant frequently or primarily cooks with peanut oil, a peanut allergy may be listed as a dietary restriction).

A food lookup list may include food items that are grown locally in the user's area and/or that are in season. In some implementations, the food lookup list may be dynamically updated based on changes to the user's location.

A reminder or notification lookup list may include a number or predetermined messages or portions of predetermined messages such as a blood glucose testing reminder message or a portion of a blood glucose reminder message (e.g., "Please test your blood glucose now."), a medical provider notification or reminder message or a portion of a medical provider notification or reminder message (e.g., "Remember to call your Doctor this week" or "Your Doctor [name field] will be calling you shortly."), an emergency services notification message or portion of an emergency services notification message (e.g., "An ambulance is on the way to your location."), a shipment notification or reminder message or a portion of a shipment notification or reminder message (e.g., "Your shipment of blood glucose strips has arrived" or "Don't forget to order your blood glucose testing strips.") an exercise reminder message or a portion of an exercise reminder message (e.g., "It's a great time for a run!"), a dietary reminder message or a portion of a dietary reminder message (e.g., "You haven't had anything to eat in the last six hours, here are some great restaurants in your area: [restaurant field(s)].").

The fields of the lookup lists may be automatically filled in by the assistant server system 120 based on, for example, data acquired from an external server (e.g., weather server, a server containing restaurant information for a specific area or multiple areas, a server containing food information about food that is grown locally in a specific area or multiple areas, etc.), and data acquired from the user device 110 or another computing device of the user (e.g., location data, elevation data, temperature data, self-reported data such as dietary restrictions, etc.).

Each option in the lookup list may include particular conditions or requirements that define the message or portion of the message that should be selected. For example, with respect to a weather lookup list, the conditions or requirements for selecting a good weather message may include, for example, that it is, or will be with at least some confidence (e.g., 70% chance or higher), sunny or partially sunny, and it is, or will be with at least some confidence, at least 60 degrees outside. As another example, with respect to a restaurant or food lookup list, the conditions or requirements may include a requirement that the user not have certain dietary restrictions (e.g., peanut allergy, tree nuts allergy, gluten intolerance, lactose intolerance, etc.). The dietary restrictions may be self-reported by the user (e.g., in response to the assistant server system 120 requesting the information) or may be automatically pulled by the assistant server system 120 from the medical provider/EMR system 140 (e.g., after the user has consented to such information sharing).

In generating a message and/or a recommendation, the system 100 (e.g., the assistant server system 120), may use one or more templates. The templates may include various fields where acquired or generated data may be added. Some of the fields may correspond to data that is to be obtained from a look up list. Some of the fields may correspond to data that is acquired from one or more external servers (e.g., a weather server, a server containing restaurant information for a specific area or multiple areas, a server containing food information about food that is grown locally in a specific area or multiple areas, etc.). Some of the fields may correspond to data that is acquired from the user device 110 and/or one or more other computing devices of the user (e.g., location data, elevation data, temperature data, etc.).

As an example, in generating a recommendation for the user that "You should call your doctor" the assistant server system 120 performs the following actions: the assistant server system 120 monitors the user's blood glucose levels (e.g., acquired from the glucometer 190 and/or self-reported by the user through the user device 110 or another computing device of the user); the assistant server system 120 compares the user's monitored blood glucose levels with one or more thresholds (e.g., that may be based on the user's characteristics and/or behaviors; that may be blood glucose level thresholds and/or timing thresholds); the assistant server system 120 determines that the user's monitored blood glucose levels exceed a threshold of the one or more thresholds and/or that the assistant server system has not received blood glucose test data within a threshold amount of time; based on the determination, the assistant server system 120 determines that a message should be generated; the assistant server system 120 accesses a message template from a listing of message templates based on one or more messaging factors, the message template having one or more message fields; the assistant server system 120 fills in the message fields to generate a message, the message fields are filled in using data acquired from the user device 110, the glucometer 190, a different computing device of the user, the medical provider/EMR system 140, and/or another external server system; and the generated message is sent to the user, a medical provider of the user, and/or emergency services. The messaging factors may include the one or more thresholds exceeded or elapsed, the time of day (e.g., time of day when the one or more thresholds were exceeded or elapsed), the current blood glucose level of the user, the current or expected weather, a percentage or amount that the blood glucose levels exceeded the blood glucose threshold, an amount of time that has passed since the assistant server system 120 received a blood glucose testing result, and/or the like.

The user may submit the request/query 115 to the system 100 through the digital assistant on the user device 110. In the preferred embodiment, the request/query 115 is sent to the assistant server system 120 which produces a transcription of the request/query 115 for analysis. The user may ask or request, for example, "What is my most recent blood glucose reading?" "When will my new shipment of testing strips arrive?" "Please contact my coach," "Please contact my doctor," or "Please call 911!" The user may also ask or request to schedule a call with their coach or doctor. In response to receiving a query or request 115, the system 100 analyzes the request/query 115 and determines an action to take. For example, one action may include selecting a message to send to the user, i.e., providing a response 125. Another action may be contacting the user's medical coach, the user's doctor, or emergency services. For example, if the system 100 receives the query, "What is my most recent blood glucose reading?" The system 100 may respond, "Your most recent blood glucose level was 80 milligrams per deciliter."

In some implementations, the system 100 (e.g., through the assistant server system 120), takes multiple actions in response to receiving the request/query 115. For example, if the user submits a request, "I need to go to the hospital!", the assistant server system 120 may automatically contact emergency services 160 and send the user a message or other notification to their user device 110 (and/or to a one or more other computing devices) confirming that emergency services 160 have been contacted, that emergency services 160 are in route, and/or that emergency services 160 have arrived at their location (e.g., their GPS location based on data provided by a GPS unit in the user device 110 or based on data provided by a GPS unit in a different computing device, based on a listed home address for the user, or the like).

In some situations, the system 100 can provide the user with a push notification (e.g., a message). These notifications differ from responses in that they are not a direct reaction to a user's query. These notifications can be triggered in a number of different ways. One way a notification can be triggered is in response to the user submitting data to the system 100 through the digital assistant. The data may include, for example, blood glucose testing results submitted by the user. In such a situation, the user's current blood glucose test results would be compared to predetermined blood glucose thresholds. If the user's test results are below or above the predetermined threshold, the system 100 can determine a message to communicate to the user and the user will be receive the message through a notification. If the results are above the predetermined threshold, the notification message might read for example, "Your glucose level is too high." If the results are below the predetermined threshold, the notification message might read for example, "Your glucose level is too low."

As discussed above, the predetermined blood glucose thresholds may be based on the user's characteristics and/or behaviors. In other words, the thresholds used for triggering communications with users and/or generating message content can be personalized or customized for individual users. For example, the assistant server system 120 may generate these one or more blood glucose thresholds based on a weight of the user, an age of the user, the sex of the user, the average blood glucose level of the user, the average blood glucose level of the user for a given time of day (e.g., morning, afternoon, night, etc.), the average blood glucose level of the user for the time of year (e.g., spring, summer, fall, or winter), behaviors of the user (e.g., how often or consistently the user provides data such as blood glucose test results through the glucometer 190), historic glucose levels for the user and/or for others having matching or similar characteristics and/or behaviors of the user, the fitness of the user, and/or the like. The assistant server system 120 may generate these one or more blood glucose thresholds based on data it receives from the glucometer 190, the user device 110, one or more other computing devices of the user, the medical provider/EMR system 140, stored historical data of the user, and/or stored historical data of other users (e.g., other users having characteristics and/or behaviors similar to the user or matching the user). The assistant server system 120 may update these blood glucose thresholds of the user over time, e.g., based on changed characteristics or behaviors of the user.

In some implementations, the server system 120 uses a set of prior glucose test results to set one or more customized thresholds for a user. Each user's pattern or trend of measurements can be used to set adaptive (e.g., automatically adjusted) personalized thresholds for issuing warnings and taking other actions. For example, the history of previous measures for a user can be used to generate baseline upper and lower thresholds representing acceptable levels. Just before mealtime, blood glucose levels may be around 60 mg/dL for some users or around 90 mg/dL for others. For a user whose levels typically do not fall below 90 mg/dL, a reading of 60 mg/dL may trigger an alarm or notice to a doctor or coach. On the other hand, for a user whose readings typically reach 60 mg/dL, the server system 120 would not consider this level to require action. For each user, the server system 120 may adjust the thresholds over time based on the glucose test results received. For example, if the user's typical measures gradually increase from one month to the next, the system may make increases to the user's thresholds to align with the current trend. The system can do this in various ways, such as detecting a change in the user's pattern of results and altering the threshold in response. As another technique, the system may averages of test results over a time period (e.g., the last 3 months) to set the thresholds, so the threshold is newly calculated over a different set of measurements from time to time.

Beyond simply looking at measurement result values, the server system 120 may also take into account the user's specific pattern and trend of measurements. For example, each user may have different typical mealtimes, different levels of consistency in testing and eating, and so on. Rather than simplify the user behavior into one set of thresholds, the server system 120 may identify ranges that may vary throughout the day, or from one situation to another. For example, the threshold used to generate message content (e.g., to classify a user's glucose level as acceptable or not, or to suggest an action to the user) may vary according to the time of day, according to an equation, machine learning model, curve, or other representation of the user's pattern.

In other embodiments, the system 100 may send the user a notification through the digital assistant if a certain amount of time has elapsed since the user last submitted blood glucose data. Such a push notification will serve as a reminder for the user to test their blood glucose level. This time threshold will normally be different for each user, as it will be based on their blood glucose testing and/or submission frequency in the preferred embodiment of the present invention. Therefore, for example, the amount of elapsed time needed in order to trigger a reminder notification for one user who tests their blood glucose level ten times a day (if, for example, they suffer from Type 1 diabetes) may be one-fifth of that needed to trigger a reminder notification for another user who tests their blood glucose level twice a day (if, for example, they suffer from Type 2 diabetes). As stated above, this timing threshold may be based on the frequency of a user testing their blood glucose level and/or how often a user submits their blood glucose level to the system 100 through the digital assistant. The system may acquire the user's testing frequency from a medical provider/EMR system 140, or through self-reporting by the user. The system 100 may also estimate a user's testing frequency based their submission frequency of test results.

In some implementations, the timing threshold correlates with one or more skipped testing submissions. For example, if a user's testing frequency is ten times throughout twelve hours of a given day and the timing threshold is correlated to two skipped testing submissions, the timing threshold would equal 12/10*2 hours, i.e., two hours and twenty-four minutes. As such, the assistant server system 120 would send the user a notification, e.g., to their digital assistant on the user device 110 or to a different computing device, reminding the user to test their blood glucose level once it determines that two hours and twenty-four minutes have elapsed since the user last submitted test results or since the twelve hour testing period of the day began. For example, if the twelve hour testing period began at 8:00 am and if the assistant server system 120 does not receive any test results, then the assistant server system 120 may send a notification to the user at 10:24 am. An example notification message that can be sent by the assistant server system 120 in response to the time threshold elapsing may read, "Please test your blood sugar now."

In some implementations, where a skipped testing submission is actually due to a lack of communication between the glucometer 190 and the assistant server system 120 (e.g., due to having no cellular service or internet connection), the system 100 requests information from the user. For example, the assistant server system 120 may determine that the user device 110 no longer has network connectivity or is in an off state, e.g., by pinging the user device 110. In response to determining the user device 110 no longer has network connectivity or is in an off state, the assistant server system 120 may send a notification or a message to another computing device of the user asking them for information or providing instructions. The notification or message may be sent to the user once the assistant server system 120 determines that a timing threshold has passed, e.g., since the assistant server system 120 determined that the user device 110 lost connectivity or was in an off state, since the assistant server system 120 last received blood glucose results of the user, since the assistant server system 120 was scheduled to receive blood glucose results of the user, or the like. In some implementations, the system 100 recognizes that the communication between glucometer 190 and the server system has been severed and, based on the recognition, the system 100 will prevent the timing threshold from running until communication is reestablished.

The instructions provided to the user may include, for example, instructions for the user to immediately test their blood glucose level, to test their blood glucose level within a time period (e.g., the next fifteen minutes, the next thirty minutes, the next hour, etc.), to go to the hospital, to contact their doctor, or the like.

The information requested may include, for example, a confirmation of whether the user has tested their blood glucose within a certain time frame (e.g., the past hour, past two hours, past three hours, etc.), a time when the user last tested their blood glucose level, and/or the blood glucose level of the user when they last tested. Based on the information received, the assistant server system 120 may perform additional actions such as, for example, instructions to test their blood glucose again, contact emergency services, contact a doctor or the user's specified doctor, provide the information (or a portion of the information) to the medical provider/EMR system 140, or the like.

In some implementations, the timing threshold is a fixed amount of time that begins running once the system 100 recognizes a missed test submission. For example, the timing threshold might be set to three hours. In that case, if the system 100 expects a test submission at 8:00 am, then the system 100 (e.g., through the assistant server system 120) may send a notification to the user at 11:00 am.

In some implementations, reminder notifications need not correlate with a missed test submission. In such embodiments, the frequency of reminders can be set by the system 100 or by the user. For example, the user may set two reminders a day, one in the morning and one at night. The user can create such a setting through the digital assistant. If set by the system 100, the frequency of reminders may be standard for all users or may be tailored for each particular user. For example, if standard for all users, the system 100 may remind each user once a day to test their blood glucose level. If reminders are tailored for each particular user, the system 100 may look at how often a user is supposed to test their blood glucose level. For example, if one user is supposed to test their blood ten times a day and another user twice a day, then the system 100 may send (e.g., through the assistant server system 120) the first user five reminders a day and the second user one reminder a day.

The system 100 may provide other push notifications. The system 100 may send the user a push notification when the system 100 has contacted the user's coach, the user's doctor, or emergency services. The system 100 may also notify the user when they can expect their next shipment of blood glucose testing strips, or when such strips have been shipped. Such a notification message may read, "Good news, your next shipment of 200 strips has shipped, and will arrive on Tuesday." The system 100 could send push notifications of recommendations. Such recommendations could include cookbooks for those with diabetes, food recommendations, and action steps to lower blood glucose levels. Such recommendation notifications may be sent to users who are determined by the system 100 to be at risk or almost at risk based on the user's blood glucose testing data and/or the user's responses to one or more system surveys.

The push notification messages and response messages may be presented in audible form and outputted through the user device 110 by the digital assistant. In other embodiments, the user is notified of the messages through text appearing on a screen of the user device 110, or through a combination of sound and text. In other embodiments, the user is notified of the messages through a glowing light on the user device 110.

As discussed above, the system 100 (e.g., the assistant server system 120) may need to determine a message to send to the user in response to a query or request, or when creating a push notification. The system 100 may also determine a message to send to the user's coach, to the user's doctor, or to the emergency services 160 if the system 100 determines that they need to be contacted. As discussed above, when a user makes a query or a request, the server system transcribes the user's query or request for analysis. Once transcribed, an AI system located within the assistant server system 120 analyzes the transcribed data and chooses a message or other notification to send to the user, to the user's coach, to the user's doctor, and/or to the emergency services 160, e.g., if the system 100 determines that such contact is necessary. In situations where the system 100 is sending a push notification in response to receiving blood glucose testing results, the AI system may take those results, compare them with the one or more predetermined thresholds and determine a message to send to the user, to the user's coach, to the user's doctor, and/or to the emergency services 160, e.g., if the system 100 determines that such contact is necessary. In situations where the system 100 is sending a push notification in response to a timing threshold elapsing, the AI system may determine a message to send to the user, to the user's coach, to the user's doctor, and/or to the emergency services 160, e.g., if the system 100 determines that such contact is necessary. In situations where the system 100 is sending a push notification in response to a preset reminder to the user, the system 100 may not need to use the AI system as the message for such reminders is predetermined. However, an AI system may be used in such a situation to determine if one or more of the reminders are ignored and determine a message to send to the user, and/or to the contacts mentioned above (e.g., coach, doctor, and/or the emergency services 160) based on the number of ignored reminders.

In some implementations, the system 100 includes multiple AI systems. For example, the system 100 may include a first AI system that is and/or is part of the digital assistant on the user device 110, and a second AI system that is part of the assistant server system 120.

The AI system may leverage one or more machine learning models or networks. For example, the machine learning model(s) of the AI system can include neural network, a classifier, a decision tree, a support vector machine, a regression model, a nearest neighbor method such as K-means or K-nearest neighbor, a dimensionality reduction algorithm, or a boosting algorithm. The machine learning model(s) can be trained using supervised learning based on a training data set that includes various examples of input values representing situations or contexts, and outputs representing desired outputs that can be used as training targets.

Alternatively, the AI system may leverage one or more programmed algorithms or sets of rules in place of one or more machine learning models or networks.

The system 100 also provides an on-demand platform for filling blood glucose testing strips. The system 100 will forecast an order size, order the testing strips in the amount forecasted, and ship those testing strips to the user based on verified usage. In the preferred embodiment, usage is verified when the user submits testing data. Usage may also be verified by the user after-the-fact. For example, if a user submits blood sugar test results ten times a day, then the verified usage would be ten per day, or seventy per week.

The system 100 can schedule shipments at varying intervals or at different intervals for different users based on client pharmacy benefit design, e.g., every week, every two weeks, or every month. As an example, the system 100 may fill an order of 140 testing strips and ship those to the user if the shipment is planned for every month. The system 100 may adjust the size and/or timing of future shipments based on changes in the user's verified usage of test strips. The system 100 may inform the user through the digital assistant that testing strips are being filled and/or shipped through use of push notifications or in response to a user's query. The system 100 may also inform the user through a messaging system that informs the user that there are saved, unread messages. In such an example, the user device 110 may indicate that the user has saved, unread messages by having an LED or other element on the user device 110 provide a visual output. The LED might glow a certain color to indicate messages, e.g., glows green.

The system 100 may also contract those other than the user, such as the user's medical coach, the user's doctor, or emergency services. Contact may be initiated when a user's blood glucose level falls outside of a predetermined threshold. There may be more than one predetermined threshold. For example, there may be a first threshold that is smaller than a second threshold. When the user's blood glucose level is outside of the first threshold but within the second, the user may be notified that their blood glucose level is too high or too low, however, no contact is initiated. If the blood glucose level is outside of both thresholds, then the system 100 may contact the user's medical coach, the user's doctor, and/or emergency services. In some implementations, there is a third predetermined threshold. If the blood glucose level falls outside of the first two thresholds but within the third threshold, then the user's medical coach will be contacted, however, the user's doctor and emergency services will not be contacted. If the blood glucose level falls outside of all three thresholds, then the system 100 may contact the user's doctor and/or emergency services in addition to or in lieu of the user's medical coach. In some implementations, there is a fourth predetermined threshold. If the blood glucose level is outside of the first three thresholds but within the fourth threshold, then the user's doctor and/or medical coach will be contacted, however, emergency services will not be contacted. If the blood glucose level falls outside of all four thresholds, then the system 100 may contact the emergency services in addition to or in lieu of the user's doctor and/or medical coach.

The system 100 may also contact others in additional situations. The system 100 may contact the user's medical coach or the user's doctor if the user has not submitted test results in a certain amount of time. Such amount of time may be, for example, five days. Similarly, the system 100 may contact the user's medical coach, the user's doctor, or emergency services if the system 100 has not heard from the user in a certain amount of time, i.e., the user has submitted no data, has not responded or acknowledged notifications, and has made no queries.

Once the system 100 contacts the user's coach, the user's doctor, or emergency services. The system 100 may allow the coach, doctor, or emergency services to contact the user through the digital assistant on the user device 110. This has benefit of better ensuring the safety of the user incase the system 100, coach, doctor, or emergency services does not have the current phone number for the user, in case the user does not have cell phone coverage in their current location, or in case the user is not near their phone.

The system 100 may provide incentives to encourage the user to consistently test their blood glucose level and report the results. One way that the system 100 can incentivize this behavior is through a point system. Through a point system, the user will earn points when they report their blood glucose level. The point system can be designed such that a user only earns points or earns additional points if they test their blood glucose level the correct amount of times per day and report all test results to the system 100. Users can also earn points for certain milestones. These milestones can be the utilization of a system feature that they had yet to use. Other milestones could include a user submitting all of their test results, or a high percentage of their test results, for a given period of time, such as two days, a week, a month, a year, etc. The system 100 may also implement gamification in order to incentivize the user. For example, the system 100 might allow a user to guess what their next blood glucose reading will be. If the member responds, the digital assistant will record the reading and the system 100 will determine a message to send to the user through the digital assistant based on how close their guess was to their actual results. If the user's guess was within 20% of their actual reading, for example, the digital assistant may respond with, "You were close, your reading was actually 123." In some implementations, a user earns points through playing the game. For example, if a user's blood glucose level guess is within 10% of the actual reading, the user will earn additional points.

In some implementations, the data provided to the assistant server system 120, e.g., from the user device 110 or the glucometer 190, is encrypted. For example, blood glucose test results of the user may be encrypted at the user device 110 or at the glucometer 190 prior to being sent to the assistant server system 120.

In some implementations, the data provided to the back-end server 130, e.g., from the assistant server system 120, is encrypted. For example, blood glucose test results of the user may be encrypted at the assistant server system 120 prior to being sent to the back-end server 130.

Figure 2A:
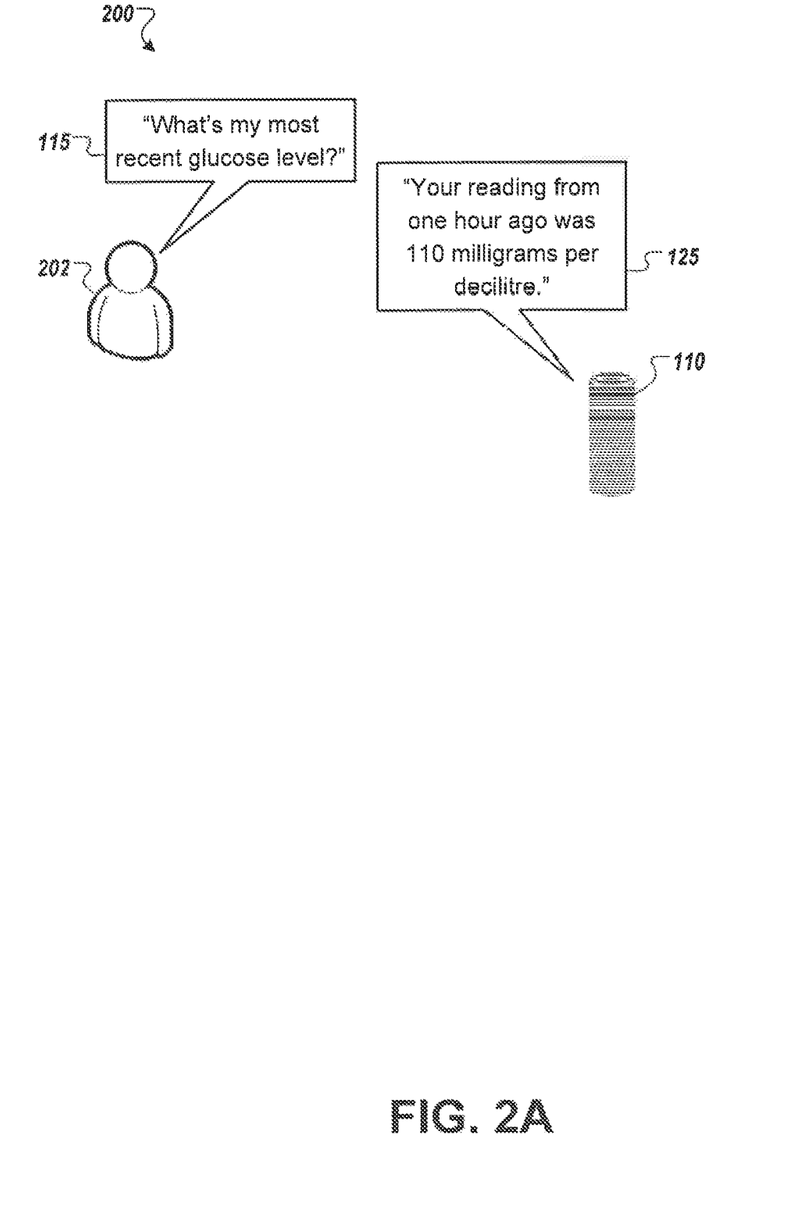
FIGS. 2A-2C are diagrams that illustrates an example interaction between the user and the digital assistant.

FIG. 2A is a diagram that illustrates an example interaction 200 between the user 202 and the digital assistant on the user device 110. This interaction is specifically the request/query 115 provided by the user 202 and a response 125 provided by the digital assistant on the user device 110. In this example, the user submits the request/query 115 to the digital assistant on the user device 110. Here, the user 202 has asked and the request/query 115 includes, "What's my most recent glucose level?" The system 100 (as shown in FIG. 1) determines a message to send to the user 202 through the digital assistant on the user device 110. This response 125 is then outputted from the user device 110. Here, the response 125 reads, "Your reading from one hour ago was 110 milligrams per deciliter."

Figure 2B:
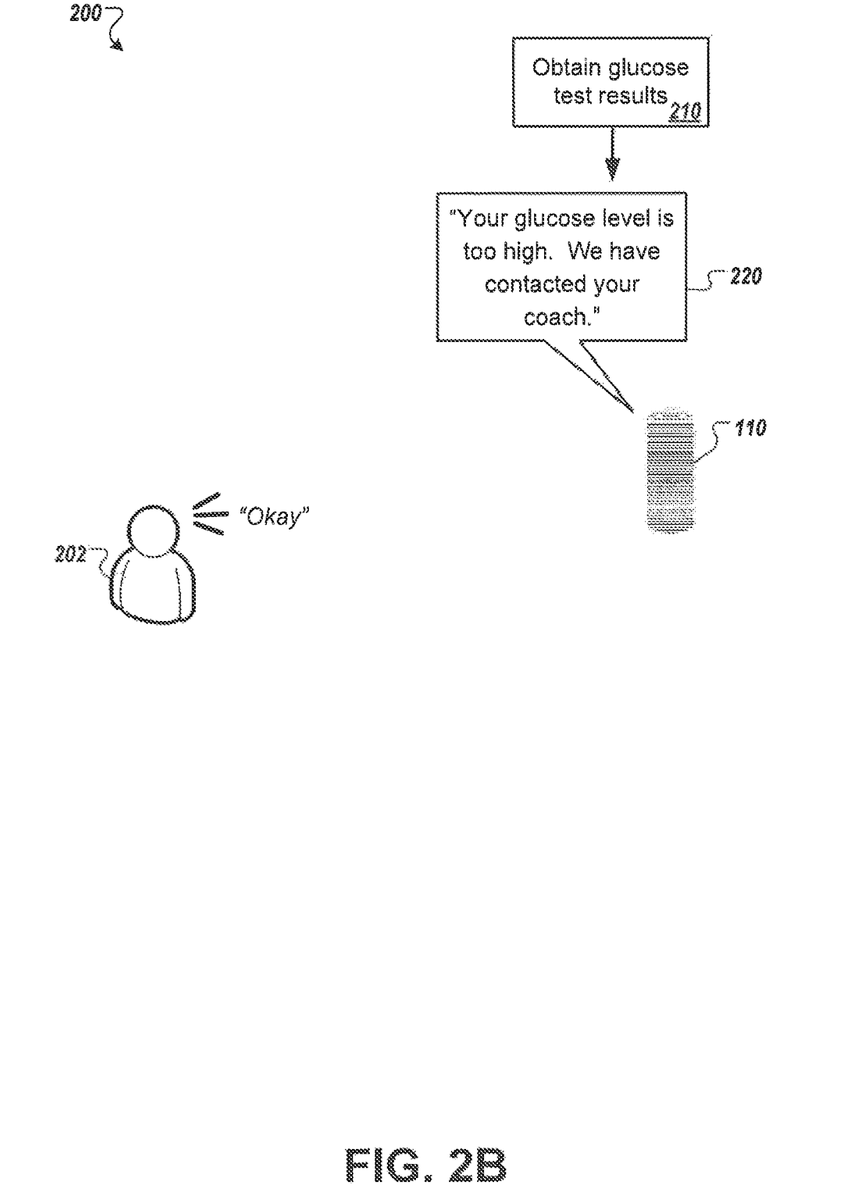

FIG. 2B is a diagram that illustrates an example interaction 200 between the user 202 and the digital assistant on the user device 110. This interaction is specifically a push notification 220. In this example, the user 202 has submitted a blood glucose level result. The system 100 (as shown in FIG. 1) then determines that it has obtained blood glucose level data 210, compares that data with predetermined threshold data, determines that the blood glucose level data exceeds the threshold level, and determines a message to send to the user 202 through the digital assistant on the user device 110. This push notification 220 is then outputted from the user device 110. Here, the push notification 220 reads, "Your glucose level is too high. We have contacted your coach." In this example, the system 100 (as shown in FIG.

1) has also taken the action of contacting the user's medical coach based on the submitted test result data.

Figure 2C:
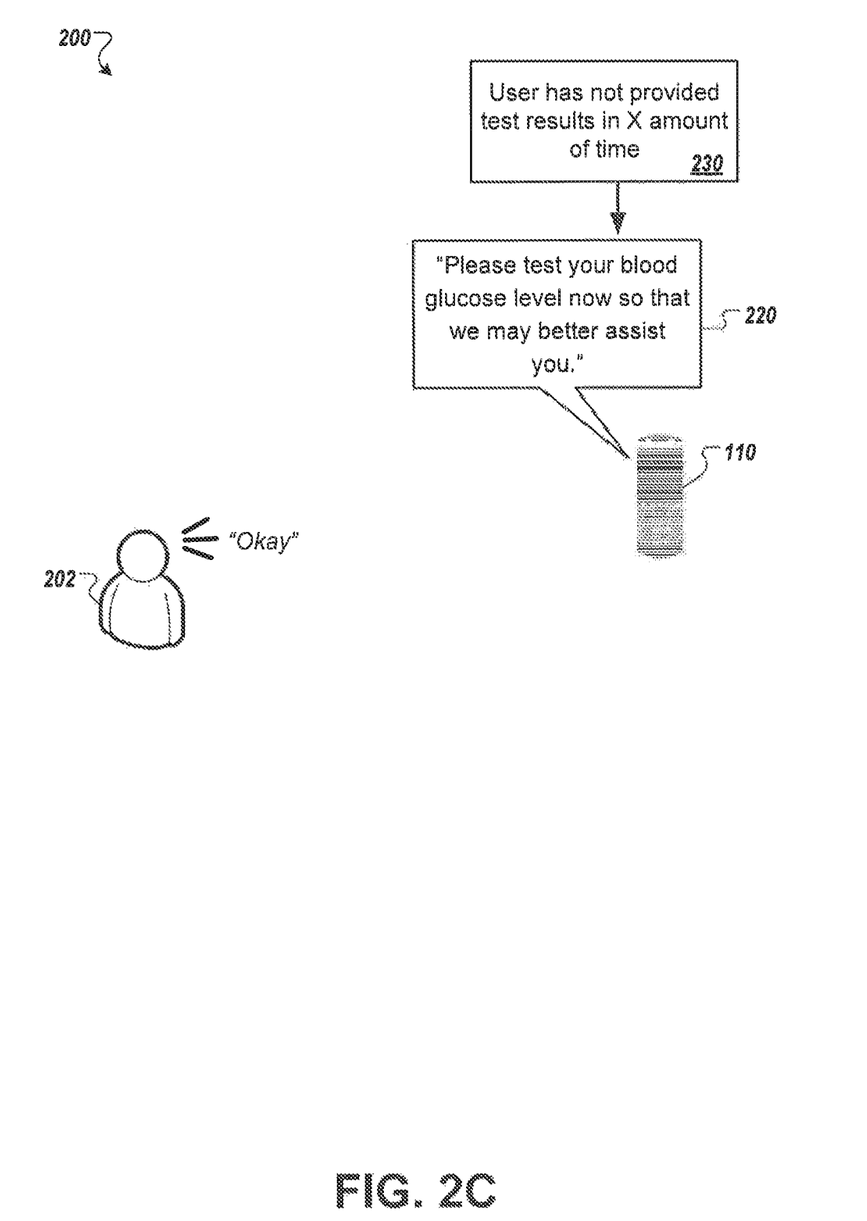

FIG. 2C is a diagram that illustrates an example interaction 200 between the user 202 and the digital assistant on the user device 110. This interaction is specifically a push notification 220. In this example, the user 202 has not submitted a blood glucose level result in X amount of time. The system 100 (as shown in FIG. 1) determines that X amount of time has passed since the user 202 has submitted any test results 230, that X amount of time is compared with threshold data for timing, and that X amount of time exceeds the threshold level for trimming, and determines a message to send to the user 202 through the digital assistant on the user device 110. This push notification 220 is then outputted from the user device 110. Here, the push notification 220 reads, "Please test your blood glucose level now so that we may better assist you."

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

The invention claimed is:

1. A system comprising:
   a server system comprising one or more computers, the server system being configured to store measurement data obtained for a user from a sensing device;
   a sensing device associated with the user, the sensing device being configured to automatically send measurement data to the server system indicating that a measurement has been performed and indicating results of the measurement; and
   a client device associated with the user, the client device providing a voice interface to the user;
   wherein the server system is configured to perform operations comprising:
      obtaining text of an utterance received by the client device through the voice interface,
      generating a response to the utterance based on the measurement data; and
      providing data indicating the response to cause a synthesized speech response to be provided to the user through the client device.

2. The system of claim 1, wherein obtaining the text of the utterance comprises:
   obtaining, over a communication network, a transcription of the utterance generated through automatic speech recognition performed by a third-party voice processing server.

3. The system of claim 1, wherein the operations comprise:
   storing, by the server system, data that indicates a coach assigned to assist the user;
   identifying, based on a presence of one or more keywords in the utterance, determining an electronic address for the coach assigned to assist the user; and
   in response to receiving the data indicating the utterance, initiating a call between a device associated with the coach and a device associated with the user.

4. The system of claim 1, wherein the operations comprise causing, by the server system, the client device to output a prompt to the user;
   obtaining data indicating a transcription of a spoken response to the prompt;
   extracting, from the transcription, data indicating one or more of a measurement time, a measurement result, a symptom experienced by the user or a mood of the user; and
   updating records for the user based on the extracted data.

5. The system of claim 1, wherein the sensing device is a glucometer, and wherein the measurement data indicates use of a glucose testing strip and indicates results of glucose testing.

6. The system of claim 5, wherein the operations comprise:
   storing data indicating a predetermined set of milestone conditions related to glucose testing;
   determining, based on stored glucose testing records for the user, that at least one of the predetermined set of milestone conditions has occurred; and
   based on determining that at least one milestone condition of the milestone conditions has occurred, providing an incentive corresponding to the at least one milestone condition.

7. The system of claim 5, wherein the operations comprise:
   determining a time for glucose testing for the user;
   determining that the server system has not received an indication of a glucose test for the determined time; and
   based on determining that the server system has not received an indication of a glucose test for the determined time, initiating a message to the client device that reminds the user to perform a glucose test.

8. The system of claim 7, wherein determining the time comprises determining the time based on an estimate of mealtimes for the user or a history or pattern of glucose testing times for the user.

9. The system of claim 5, wherein the operations comprise:
   receiving data indicating a blood glucose level determined using the glucometer;
   determining that the blood glucose level is outside a range; and
   in response to determining that that blood glucose level is outside the range, initiating a communication to a coach, medical service provider, or emergency response provider.

10. The system of claim 5, wherein the operations comprise:
    accessing data indicating a treatment regimen that includes one or more medications prescribed for the user;
    determining that the server system has not received data indicating a needed glucose test for the user; and
    in response to determining that the server system has not received data indicating a needed glucose test for the user, providing a message the reminds the user to take the one or more medications according to the treatment regimen or asks the user whether the user took the one or more medications.

11. The system of claim 5, wherein the text of the utterance includes data indicating a time of glucose test and/or a result of a glucose test, and wherein the operations including updating glucose testing records for the user, based on the text of the utterance to indicate the glucose test and/or result of the glucose test.

12. The system of claim 5, wherein the operations comprise:
   storing data indicating a threshold period of time for glucose testing for the user;
   determining that glucose testing has not occurred for a time period of at least the threshold period of time; and
   in response to determining that glucose testing has not occurred for a time period of at least the threshold period of time, initiating an interactive voice communication with the user through the client device.

13. The system of claim 12, wherein the interactive voice communication is a call to a medical professional or a call with an automated voice response system using the voice interface.

14. The system of claim 12, wherein the threshold period of time is customized for the user based on the stored data indicating the user's history of glucose testing.

15. The system of claim 5, wherein the operations comprise:
   evaluating the stored data indicating glucose testing history of the user to determine one or more patterns in timing of glucose testing by the user;
   determining that a length of time since a most recent glucose test deviates from the one or more patterns;
   in response to determining that the length of time since the most recent glucose test deviates from the one or more patterns, initiating a message to the user through the client device.

16. The system of claim 15, wherein the operations comprise:
   determining that a glucose reading for the user exceeds a threshold, wherein the threshold is a predetermined threshold or a threshold that is customized for the user; and
   in response to determining that the glucose reading for the user exceeds a threshold, performing at least one of:
      initiating a call or message to a diabetes coach for the user;
      initiating a call or message to a doctor for the user;
      initiating a call or message to emergency services; or
      initiating a communication to the user that requests information about what the user ate or whether the user took a medication.

17. The system of claim 5, wherein the operations comprise:
   tracking usage of glucose test strips based on data from the glucometer indicating of testing performed by the glucometer; and
   scheduling shipments of test strips to the user, wherein timing of shipments and amount of test strips in the scheduled shipments are determined based on the tracked usage for the user.

18. The system of claim 17, wherein the operations comprise:
   providing, to a user, a message indicating an expected arrival date for a shipment of test strips and an amount of test strips in the shipment.

19. A method performed by one or more computers, the method comprising:
   receiving, by the one or more computers, measurement data generated by a sensing device associated with a user, the measurement data being sent by the sensing data automatically in response to a measurement to indicate performance of the measurement and results of the measurement;
   storing, by the one or more computers, the measurement data in association with an identifier for the user;
   obtaining, by the one or more computers, text of an utterance received of the user detected by a client device associated with the user through a voice interface provided by a client device, the text being generated by an automated speech recognizer;
   accessing, by the one or more computers, the stored measurement data associated with the user;
   in response to obtaining the text of the utterance, generating, by the one or more computers, a response to the utterance based on the text of the utterance and the stored measurement data; and
   providing, by the one or more computers, response data indicating the generated response, the response data being configured to cause a synthesized speech output to be provided to the user through the client device.

20. One or more non-transitory computer-readable media storing instructions that, when executed by one or more computers, cause the one or more computers to perform operation comprising:
   receiving, by the one or more computers, measurement data generated by a sensing device associated with a user, the measurement data being sent by the sensing data automatically in response to a measurement to indicate performance of the measurement and results of the measurement;
   storing, by the one or more computers, the measurement data in association with an identifier for the user;
   obtaining, by the one or more computers, text of an utterance received of the user detected by a client device associated with the user through a voice interface provided by a client device, the text being generated by an automated speech recognizer;
   accessing, by the one or more computers, the stored measurement data associated with the user;
   in response to obtaining the text of the utterance, generating, by the one or more computers, a response to the utterance based on the text of the utterance and the stored measurement data; and
   providing, by the one or more computers, response data indicating the generated response, the response data being configured to cause a synthesized speech output to be provided to the user through the client device.

\* \* \* \* \*